(12) United States Patent
Funaki et al.

(10) Patent No.: US 7,145,142 B2
(45) Date of Patent: Dec. 5, 2006

(54) SENSOR DEVICE WHICH DETECTS A PHYSICAL CHANGE AMOUNT OR A CHEMICAL CHANGE AMOUNT

(75) Inventors: Hideyuki Funaki, Tokyo (JP); Keitaro Shigenaka, Hachioji (JP); Yujiro Naruse, Yokohama (JP); Ikuo Fujiwara, Yokohama (JP); Naoya Mashio, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 760 days.

(21) Appl. No.: 10/306,160

(22) Filed: Nov. 29, 2002

(65) Prior Publication Data
US 2003/0113783 A1    Jun. 19, 2003

(30) Foreign Application Priority Data
Nov. 29, 2001  (JP)  ............................ 2001-363508

(51) Int. Cl.
G01J 5/24      (2006.01)
H01L 27/14     (2006.01)
H01L 31/105    (2006.01)
H03K 3/42      (2006.01)
C12Q 1/68      (2006.01)

(52) U.S. Cl. .................. 250/338.4; 257/443; 257/458; 327/515; 435/6

(58) Field of Classification Search ........ 257/E27.008, 257/E27.136
See application file for complete search history.

(56) References Cited

U.S. PATENT DOCUMENTS

| | | | | |
|---|---|---|---|---|
| 5,656,806 A | * | 8/1997 | Dautriche | ............... 250/214 R |
| 5,729,285 A | * | 3/1998 | Peterson et al. | ............. 348/162 |
| 6,300,615 B1 | * | 10/2001 | Shinohara et al. | ...... 250/214 R |
| 6,348,682 B1 | * | 2/2002 | Lee | ......................... 250/214 A |
| 6,704,050 B1 | * | 3/2004 | Washkurak et al. | .......... 348/294 |
| 6,759,657 B1 | * | 7/2004 | Iida et al. | .................... 250/332 |
| 6,809,320 B1 | * | 10/2004 | Iida et al. | ................. 250/338.4 |
| 6,956,417 B1 | * | 10/2005 | Bernstein et al. | ............ 327/157 |

OTHER PUBLICATIONS

U.S. Appl. No. 10/106,787, filed Mar. 27, 2002, pending.
U.S. Appl. No. 10/244,403, filed Sep. 17, 2002, pending.

* cited by examiner

Primary Examiner—David Porta
Assistant Examiner—Frederick F. Rosenberger
(74) Attorney, Agent, or Firm—Oblon, Spivak, McClelland, Maier & Neustadt, P.C.

(57) ABSTRACT

A sensor device includes a sensor array in which infrared sensors are arrayed and a detection circuit connected to the output signal line of the sensor array. The detection circuit includes a capacitor having a charging circuit which is selectively driven, a sense amplifier circuit which detects and amplifies a change in sensor current flowing to the output signal line, a current-to-voltage conversion circuit which converts the output current from the sense amplifier circuit into a voltage, a discharging circuit which is controlled by the output voltage of the current-to-voltage conversion circuit to discharge the capacitor, and an output circuit which outputs the terminal voltage of the capacitor.

20 Claims, 9 Drawing Sheets

SENSOR DEVICE WHICH DETECTS A PHYSICAL CHANGE AMOUNT OR A CHEMICAL CHANGE AMOUNT

CROSS-REFERENCE TO RELATED APPLICATIONS

This application is based upon and claims the benefit of priority from the prior Japanese Patent Application No. 2001-363508, filed Nov. 29, 2001, the entire contents of which are incorporated herein by reference.

BACKGROUND OF THE INVENTION

1. Field of the Invention

The present invention relates to a sensor device represented by an infrared sensor and, more particularly, to its signal detection circuit.

2. Description of the Related Art

An image sensor formed by two-dimensionally arraying infrared sensors can be used even at night. However, its sensitivity or dynamic range is poorer than that of an image sensor using visible light. For example, a monitor camera requires an NETD (Noise Equivalent Temperature Difference) of about 1 K and a dynamic range of about 30 K. It is therefore necessary to develop an infrared sensor having a higher sensitivity and wider dynamic range.

An infrared sensor array is formed by arraying a plurality of infrared sensors on a silicon substrate. Each infrared sensor is constituted by an infrared absorption section and a diode (normally formed by series connection of a plurality of diodes) serving as a thermoelectric conversion element which converts heat generated in the infrared absorption section into an electrical signal. In a bolometer non-cooled infrared sensor device, each sensor is held in a floating state to effectively transmit generated heat to the diode. Such a floating support structure is made by micromachinining technology.

Infrared rays radiated from an object are condensed by an optical lens arranged in front of the sensors and increase the temperature of the diode of each sensor. As the optical lens, a film made of a material having a high infrared transmission efficiency, for example, a Ge film is used. Assume, for example, that, a Ge lens having a transmittance of 90% and an F-number of 1.0 at a wavelength of 8 to 12 μm is used. When the surface temperature of an object changes by 1 K, the diode temperature increases by about $1 \times 10^{-3}$ K. The diode is driven such that a constant current is supplied from a constant current source. The current density J in the diode is given as a function of the temperature T, i.e., $J=Js(e^{qV/kT}-1)$, $Js=T^{3+\gamma/2} \times \exp(-Eg/kT)$, where k is the Boltzmann constant, Eg is the bandgap of silicon, and γ is a predetermined constant.

When the diode temperature increases, the voltage drop Vf of the diode decreases. Assume that when the temperature of eight diodes connected in series increases by 1K, the voltage drop Vf is about 20 mV/K. When the surface temperature of an object increases by, for example, 30 K, a potential difference of about 0.618 mV is generated as a voltage drop. When this potential difference is detected and output as a sensor output, an infrared image is detected.

In a conventional bolometer non-cooled infrared sensor, since the sensor output characteristic with respect to the change in diode temperature is not linear, it is difficult to simultaneously realize high sensitivity and a wide dynamic range.

BRIEF SUMMARY OF THE INVENTION

It is an object of the present invention to provide a sensor device having a detection circuit capable of simultaneously realizing a high sensitivity and a wide dynamic range.

The present invention may provide a sensor device for detecting a slight variation of a physical or chemical change amount, which comprises: a sensor array including a plurality of sensors, the sensor array detecting the physical change amount or chemical change amount and outputting an electrical signal; a sense amplifier circuit which amplifies the electrical signal to generate an amplified electrical signal; a current transfer circuit configured to include a first stage and a second stage, and to transfer a first current appearing on the first stage on the basis of the amplified electric signal to the second stage as a second current; a current-to-voltage conversion circuit which converts the second current to a first voltage; a first discharging/charging circuit which includes a capacitor and a first load element connected to the capacitor, and discharges/charges electric charges from/to the capacitor through the first load element on the basis of the first voltage; and an output circuit which outputs a change in voltage occurring on the capacitor according to discharging/charging of the electric charges.

The present invention may provide a sensor device for detecting a physical change amount or chemical change amount, which comprises: a sensor array including a plurality of sensors, the sensor array detecting the physical change amount or chemical change amount and outputting the electrical signal; a capacitor; a first discharging/charging circuit which is driven by a driving voltage based on the electrical signal of the sensor array to discharge/charge electric charges from/to the capacitor; a second discharging/charging circuit which charges/discharges the electric charges to/from the capacitor; a control circuit which controls the driving voltage on the basis of a potential at a node between the capacitor and the second discharging/charging circuit; and an output circuit which outputs a change in voltage occurring on the capacitor according to discharging/charging of the electric charges.

The present invention may provide a sensor device for detecting a physical change amount or chemical change amount, which comprises: a sensor array including a plurality of sensors, the sensor array detecting the physical change amount or chemical change amount and outputting an electrical signal; a sense amplifier circuit which amplifies the electrical signal to generate an amplified electrical signal; a current transfer circuit configured to include a first stage and a second stage, and to transfer a first current appearing on the first stage on the basis of the amplified electric signal to the second stage as a second current; a current-to-voltage conversion circuit which converts the second current to a first voltage; a first discharging/charging circuit which includes a capacitor and a load first element connected to the capacitor, and discharges/charges electric charges from/to the capacitor through the first load element on the basis of the first voltage; a second discharging/charging circuit which charges/discharges the capacitor; a control circuit which controls the current-to-voltage conversion circuit on the basis of a potential at a node between the capacitor and the first discharging/charging circuit; and an output circuit which outputs a change in voltage occurring on the capacitor according to discharging/charging of the electric charges.

DETAILED DESCRIPTION OF THE INVENTION

A sensor device according to an embodiment of the present invention will be described below with reference to the accompanying drawing.

Figure 1:
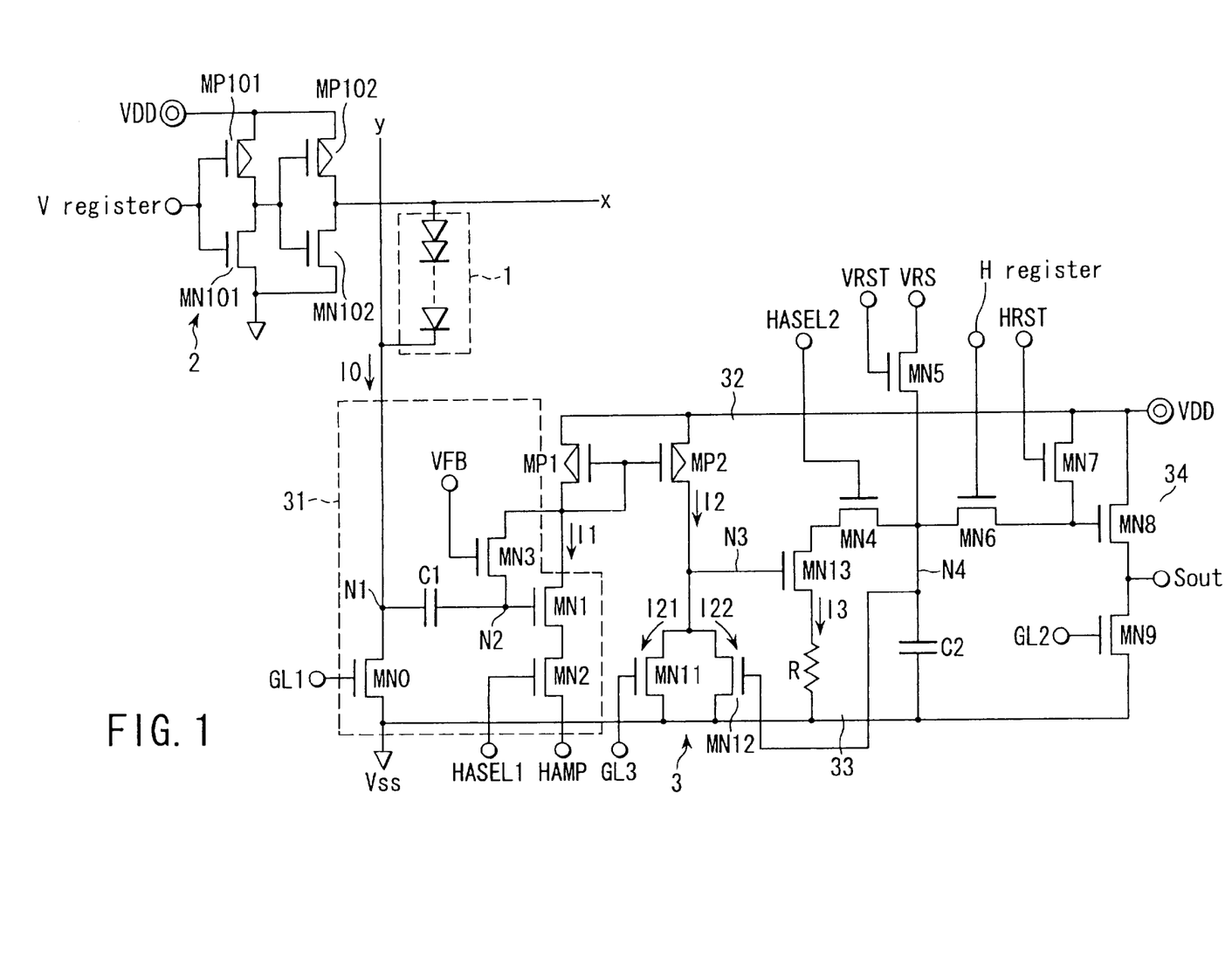
FIG. 1 is a circuit diagram showing the measurement circuit of an infrared sensor according to an embodiment of the present invention.

FIG. 1 is a circuit diagram showing the arrangement of a sensor device (bolometer non-cooled infrared sensor) according to the embodiment. A unit infrared sensor 1 of the sensor array has a diode array in which a plurality of diodes serving as a thermoelectric conversion element are connected in series. The infrared sensor 1 is arranged at the intersection between row and column selection lines x and y. The anode of the diode is connected to one selection line (driving line) x. The cathode is connected to the other selection line (output signal line) y.

Figure 2:
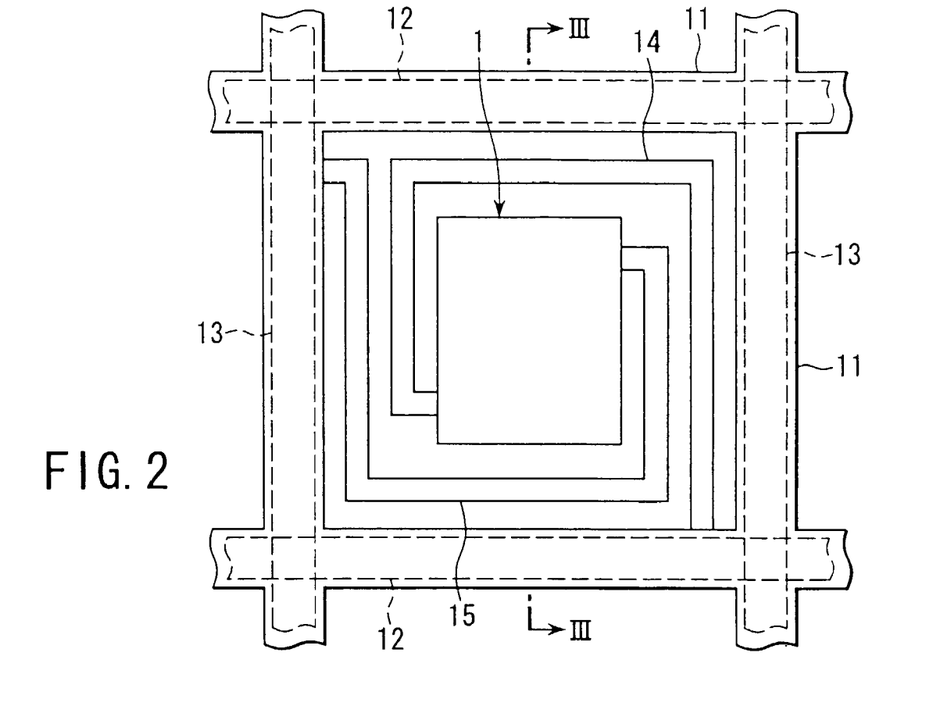
FIG. 2 is a plan view showing a unit sensor cell of the infrared sensor of the embodiment.
Figure 3:
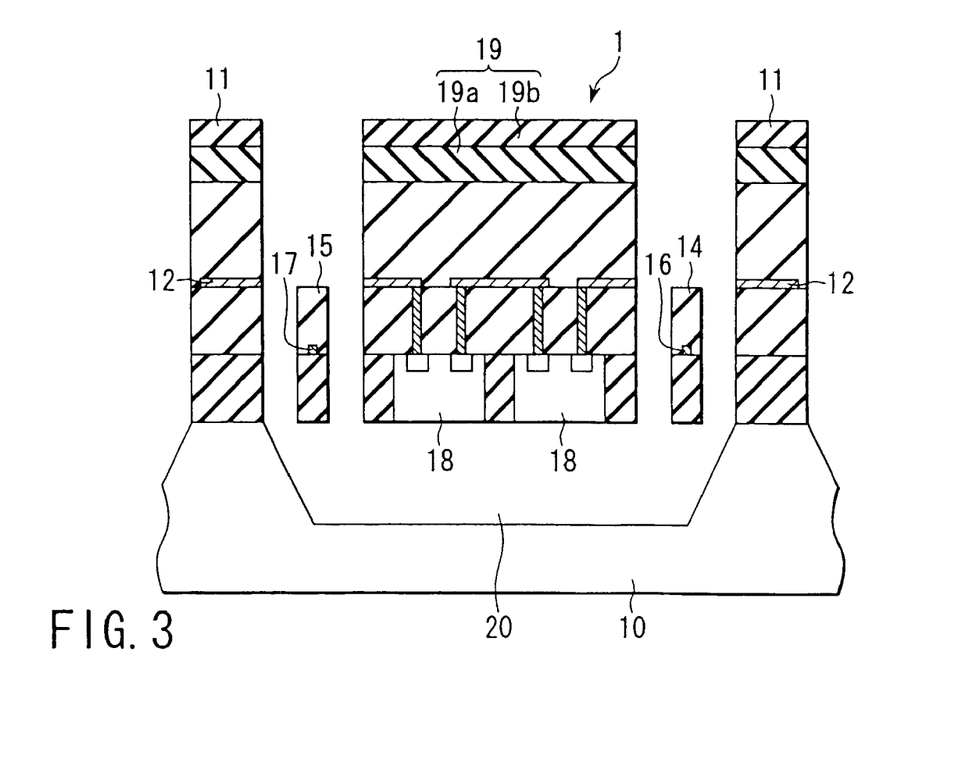
FIG. 3 is a sectional view taken along a line III—III in FIG. 2.

FIG. 2 is a plan view showing the structure of one pixel region of the sensor array section of the infrared sensor device according to this embodiment. FIG. 3 is a sectional view taken along a line III—III in FIG. 2. As shown in FIGS. 2 and 3, the sensor array has the infrared sensor 1 which is supported in a floating state above a single-crystal silicon substrate 10 serving as a semiconductor substrate via a gap 20. The infrared sensor 1 has a thermoelectric conversion element formed from a plurality of diodes 18 which are formed in a silicon layer and connected in series. The infrared sensor 1 has, at its upper portion, an infrared absorption layer 19 which has a multilayered structure of a silicon oxide film 19a and silicon nitride film 19b and is formed on the diodes via an interlayer dielectric film.

The infrared sensor 1 in the floating state is surrounded by a frame portion 11 which is fixed to the substrate 10 and in which row and column selection lines 12 and 13 (corresponding to the driving line x and output signal line y in FIG. 1) that select pixels are embedded. To connect the frame portion 11 to the infrared sensor 1 and support the infrared sensor 1 in the floating state, support beams 14 and 15 are formed above the substrate 10 in a floating state. In the support beams 14 and 15, signal wires 16 and 17 which connect the terminals of the diodes of the infrared sensor 1 to the row and column selection lines 12 and 13 in the frame portion 11 are embedded.

FIG. 1 shows a measurement circuit with a focus on one infrared sensor 1 of the sensor array. The measurement circuit is also formed on the same silicon substrate as that of the sensor array and around the sensor array. A driver 2 which drives the driving line x is constituted by two CMOS inverters to which "V register" as the output from a vertical scanning register is input. A first CMOS inverter of driver 2 is formed by transistors MP101 and MN101. A second CMOS inverter of driver 2 is formed by transistors MN102 and MP102. A detection circuit 3 which detects a change in sensor current flowing to the output signal line y has a storage capacitor C2 that is periodically precharged. One terminal of the capacitor C2 is grounded. A charging NMOS transistor MN5 which selectively charges the storage capacitor C2 is connected to the other terminal N4. When the sensor 1 is selected, the storage capacitor C2 is discharged in accordance with the output from the sensor 1 whereby the detection circuit 3 detects the sensor output.

A sense amplifier circuit 31 of current line sensing type is arranged at the first stage of the detection circuit 3. The sense amplifier circuit 31 has a load NMOS transistor MN0 connected to the output signal line y and a voltage Vss, a sense NMOS transistor MN1 which detects a voltage obtained at a terminal N1 of the output signal line y by the load NMOS transistor MN0, and the like. When a fixed bias GL1 is applied to the gate, a constant current I0 flows in the pentode region. Hence, a voltage that changes in correspondence with a voltage drop Vf of the diode of the sensor 1 is obtained at the terminal N1. The sense amplifier circuit 31 has the sense NMOS transistor MN1 whose gate is connected to the terminal N1 through a coupling capacitor C1.

A current source load PMOS transistor MP1 whose gate and drain are connected is arranged between the power supply terminal and the drain of the sense NMOS transistor MN1. The source of the NMOS transistor MN1 is connected, through an NMOS transistor MN2, to a terminal HAMP to which a control voltage is selectively applied. In sense operation, the terminal HAMP is grounded. An NMOS transistor MN3 which initially sets the gate terminal N2 of the sense NMOS transistor MN1 to a predetermined level to execute pentode operation is inserted between the drain and the gate terminal N2 of the sense NMOS transistor MN1.

To convert an output current I1 from the sense amplifier circuit 31 into a voltage, a current-to-voltage conversion circuit 32 is arranged, which has a PMOS transistor MP2 constituting a current mirror circuit together with the PMOS transistor MP1. Two NMOS transistors MN11 and MN12 are connected between the ground terminal and the drain of the PMOS transistor MP2. A fixed bias voltage GL3 is applied to the gate of one NMOS transistor MN11. The voltage at the terminal N4 of the storage capacitor C2 is fed back to the gate of the other NMOS transistor MN12.

The PMOS transistor MP2 outputs a current I2 on which the output current I1 of the PMOS transistor MP1 on the input side is reflected. If the PMOS transistors MP1 and MP2 have the same size, I1=I2. The current I2 is shunted to I21 and I22 in accordance with the conductances of the NMOS transistors MN11 and MN12. A voltage which is determined by the current lead-in capability by the NMOS transistors MN11 and MN12 and the output current I2 of the PMOS transistor MP2 is obtained at the output terminal N3 of the current-to-voltage conversion circuit 32.

An NMOS transistor MN13 having a gate connected to the output terminal N3 of the current-to-voltage conversion circuit 32 constitutes a discharging circuit 33 which discharges the storage capacitor C2. The source of the NMOS transistor MN13 is grounded through a resistance R. The drain of the NMOS transistor MN13 is connected to the terminal N4 of the storage capacitor C2 through a selection switch NMOS transistor MN4.

To extract the voltage at the terminal N4 of the capacitor C2, an output circuit 34 is arranged. The output circuit 34 is a voltage follower formed from an NMOS transistor MN8 whose gate is connected to the terminal N4 through a selection switch NMOS transistor MN6, and an NMOS transistor MN9 connected in series to the NMOS transistor MN8. A fixed bias voltage GL2 is applied to the gate of NMOS transistor MN9. A reset NMOS transistor MN7 is connected to the gate of the NMOS transistor MN8.

The operation of this sensor device can be resolved into two parts. The first is linear control of the current I3 that the discharging circuit 33 discharges in accordance with the resistance R and the driving voltage obtained from the current I2. (Note that the current I2 corresponds to the current I1.) The second is feedback control to nullify the influence of a leakage current that is generated in the charging circuit for charging the storage capacitor C2. The operation of this sensor device will be described, particularly the two parts of operation, with reference to FIG. 4.

Figure 4:
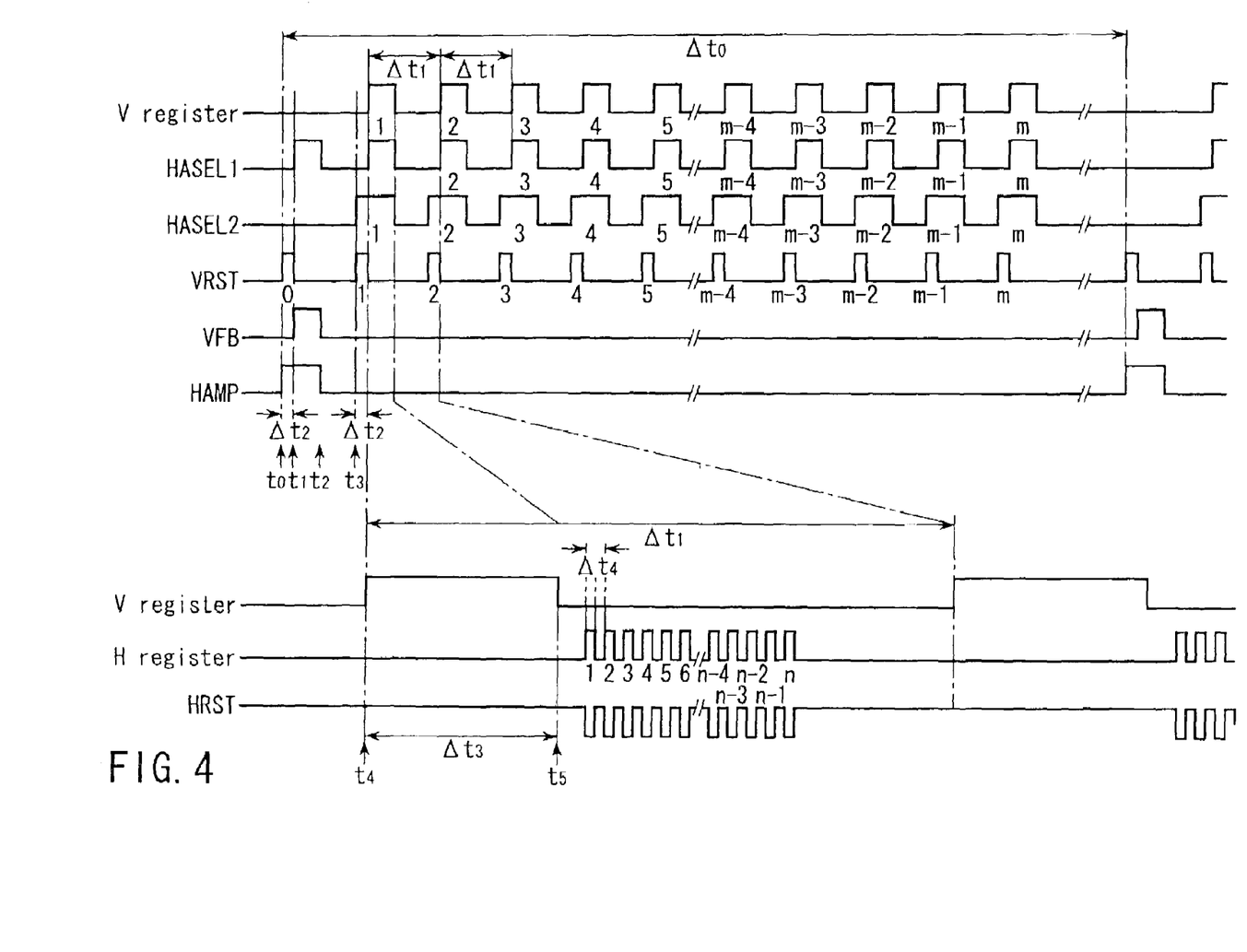
FIG. 4 is an operation timing chart of the measurement circuit of the embodiment.

FIG. 4 shows measurement operation waveforms of two-dimensional scanning when the sensor has m×n sensors. The total scanning period for m driving lines x by the output "V register" of the vertical scanning register is represented by $\Delta t0$. Horizontal scanning read is executed by the output "H register" of the horizontal scanning register to select n output signal lines for every scanning period $\Delta t1$ of each driving line x.

More specifically, the operation of one driving line x and one signal line y shown in FIG. 1 will be described. First, at time t0 at the early stage of scanning, terminals VRST and HAMP change to high level. The storage capacitor C2 is charged (reset) to a voltage VRS by the NMOS transistor MN5. The reset operation of the capacitor C2 is repeated for every vertical scanning period. When the capacitor C2 is reset, terminals VFB and HASELL change to high level while keeping the terminal HAMP at high level (time t1). Accordingly, the source of the sense NMOS transistor MN1 is boosted through the NMOS transistor MN2. The drain is almost boosted to a power supply voltage VDD. Simultaneously, the gate terminal N2 is charged by the NMOS transistor MN3.

When the terminals HAMP, VFB, and HASEL1 return to low level, the NMOS transistors MN2 and MN3 are turned off. The terminal N2 is set in the initial floating state at a predetermined voltage. The source of the sense NMOS transistor MN1 is also opened (time t2). That is, the sense NMOS transistor MN1 is set in a biased state in which the gate can execute pentode operation in the floating state. After that, the sensor 1 is driven.

First, the terminals VRST and HASEL2 change to high level (time t3). After a short time lag, "V register" changes to high level. Simultaneously, the terminal HASEL1 also changes to high level (time t4). Accordingly, the storage capacitor C2 is charged again. At the same time, the charging NMOS transistor MN13 is connected to the terminal N4 of the storage capacitor C2. The source of the sense NMOS transistor MN1 is grounded so that the sense NMOS transistor MN1 is activated. The charge operation of the capacitor C2 is ended before the NMOS transistor MN1 is activated.

The output current I0 of the sensor 1 is almost constant because the NMOS transistor MN0 is biased to the pentode region. A voltage drop $n\Delta Vf$ of the diode, which is generated by an increase $\Delta Td$ in diode temperature due to the incidence of infrared rays, is given to the gate terminal N2 of the sense NMOS transistor MN1 through the coupling capacitor C1. Let Vref be the initial set voltage of the gate terminal N2. The voltage becomes $Vref+n\Delta Vf$ due to the sensor output.

In the sense amplifier circuit 31, the current flowing to the sense NMOS transistor MN1 changes to $I1+\Delta I1$ due to the change in voltage at the gate terminal N2. Unlike a conventional circuit, the drain of the sense NMOS transistor MN1 has the current source load PMOS transistor MP1. Hence, in the sense amplifier circuit 31, class A amplification operation can be executed when the drain of the NMOS transistor MN1 falls within the range of the power supply voltage. Hence, voltage-to-current conversion with excellent linearity is performed.

In the current-to-voltage conversion circuit 32, a current $I2+\Delta I2$ on which the current of the PMOS transistor MP1 is reflected is supplied from the PMOS transistor MP2. For this reason, a voltage V2 which is determined by the current $I2+\Delta I2$ and the resistance of the NMOS transistors MN11 and MN12 is obtained at the terminal N3. The NMOS transistor MN13 of the discharging circuit 33 is driven by the voltage V2. Electric charges are removed from the storage capacitor C2 through the NMOS transistor MN4 in the ON state, the NMOS transistor MN13, and the resistance R.

Figure 5A:
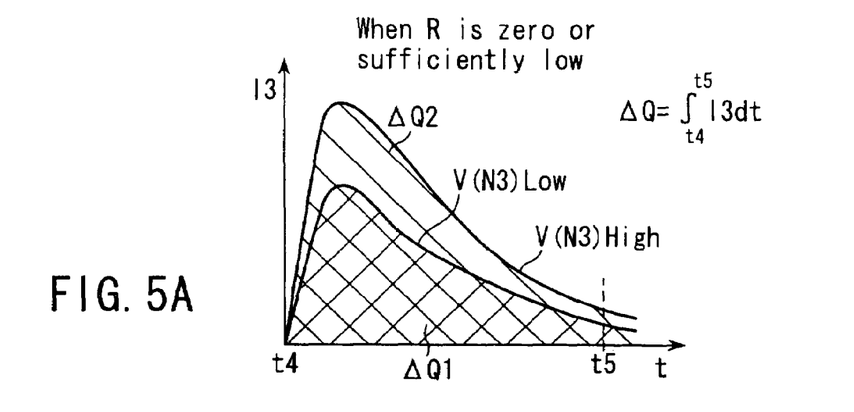
FIGS. 5A and 5B are graphs for explaining the characteristic of a discharging circuit of the embodiment.
Figure 5B:
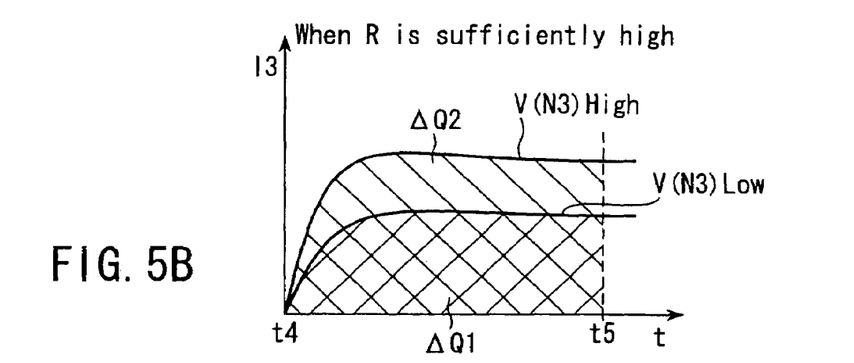

A discharge current I3 of the discharging circuit 33 changes depending on the voltage V (N3) at the terminal N3 and the voltage at the terminal N4 of the capacitor C2. FIGS. 5A and 5B show the dependence of the time-rate change in discharge current I3 and a charge change amount (i.e., discharge amount) $\Delta Q$ of the capacitor C2 on the resistance R. FIG. 5A shows a case wherein the resistance R is zero or sufficiently low. FIG. 5B shows a case wherein the resistance R is sufficiently high. When the resistance R is zero or sufficiently low, the change in discharge current I3 exhibits the waveform shown in FIG. 5A on the basis of V (N3) as a parameter. In this case, charge change amounts $\Delta Q1$ and $\Delta Q2$ of the capacitor C2 between times t4 and t5 when the sensor 1 is being driven are obtained by integrating the discharge current I3 between the times t4, and t5, though they are not always linear, as shown in FIG. 5A.

To the contrary, when the resistance R is sufficiently high, the discharge current I3 linearly changes, and the voltage V (N3) at the terminal N3 and the charge amount change $\Delta Q$ also almost linearly change, as shown in FIG. 5B. In addition, since the voltage V3 at the terminal N4 is given by $V3=VRS-\Delta Q/C$, the voltage at the terminal N4 also linearly changes. When "V register" changes to low level, and then, the "H register" changes to high level, the terminal voltage is extracted from the output circuit 34 to an output terminal Sout through the NMOS transistor MN6.

"H register" is the output from the horizontal scanning register. "H register" sequentially changes to high level, as shown in FIG. 4, so the outputs from then output signal lines y are scanned and output. In the second half of each horizontal scanning period $\Delta t4$, a horizontal scanning reset signal HRST changes to high level, and the input terminal of the output circuit 34 is reset by the NMOS transistor MN7.

The reason why the dynamic range is improved by this embodiment is as follows. In this embodiment, the sense NMOS transistor MN1 is connected to the current source load PMOS transistor MP1 to form the sense amplifier circuit 31 instead of directly discharging the capacitor C2. Hence, in the sense amplifier circuit 31, voltage-to-current conversion with excellent linearity is performed without being influenced by the terminal voltage of the capacitor C2. The output current I1 is copied by a current mirror, and converted into a voltage by the current-to-voltage conversion circuit 32 using the NMOS transistor MN11, thereby driving the discharging circuit 33. The discharge current I3 of the discharging circuit 33 is determined by the input voltage and resistance R. That is, the discharge current I3 of the discharging circuit 33 is given according to the equation Vg=V2 (which is the voltage at the terminal N3)−R×I3. Therefore, the resistance R has a function by which the drastic increase of the I3 with response to the increasing the voltage V2 (which is proportion to the current I2) at the terminal N3 is suppressed, which brings the discharge current I3 having an excellent linearity. Hence, when the output voltage linearly changes in a wide input voltage range, the dynamic range is improved.

In the sensor device according to this embodiment, the discharge current I3 is linearly controlled by the resistance R and the voltage obtained by the current-to-voltage conversion circuit 32 using a current mirror. Hence, the linearity of the sensor output can be improved without increasing the capacitance of the capacitor C2, and high sensitivity can be realized.

Additionally, in the sensor device according to this embodiment, the NMOS transistor MN12 juxtaposed to the NMOS transistor MN11 of the current-to-voltage conversion circuit 32 accelerates the voltage drop at the terminal N4. More specifically, when the voltage at the terminal N4 drops, the conductance of the NMOS transistor MN12 decreases to raise the voltage at the terminal N3. This acts to increase the discharge current of the capacitor C2 by the discharging circuit 33 and accelerate the voltage drop at the terminal N4. With this operation, the voltage at the terminal N4 of the capacitor C2 can be lowered to sufficiently low level even in a high input voltage range. Hence, the dynamic range can be widened.

Referring to FIG. 1, when the voltage at the terminal N4 of the capacitor C2 becomes low, the leakage current of the charging NMOS transistor MN5 increases. This impedes the voltage drop at the terminal N4. In the sensor device according to this embodiment, however, the capacitor C2 can be sufficiently discharged to lower the potential by the following function. That is, the NMOS transistor MN12 juxtaposed to the NMOS transistor MN11 of the current-to-voltage conversion circuit 32 accelerates the voltage drop at the terminal N4. When the voltage at the terminal N4 drops, the conductance of the NMOS transistor MN12 decreases to raise the voltage at the terminal N3. This acts to increase the discharge current of the capacitor C2 by the discharging circuit 33 and accelerate the voltage drop at the terminal N4. With this operation, the voltage at the terminal N4 of the capacitor C2 can be lowered to sufficiently low level even in a high input voltage range. Hence, the dynamic range can be widened.

Figure 6:
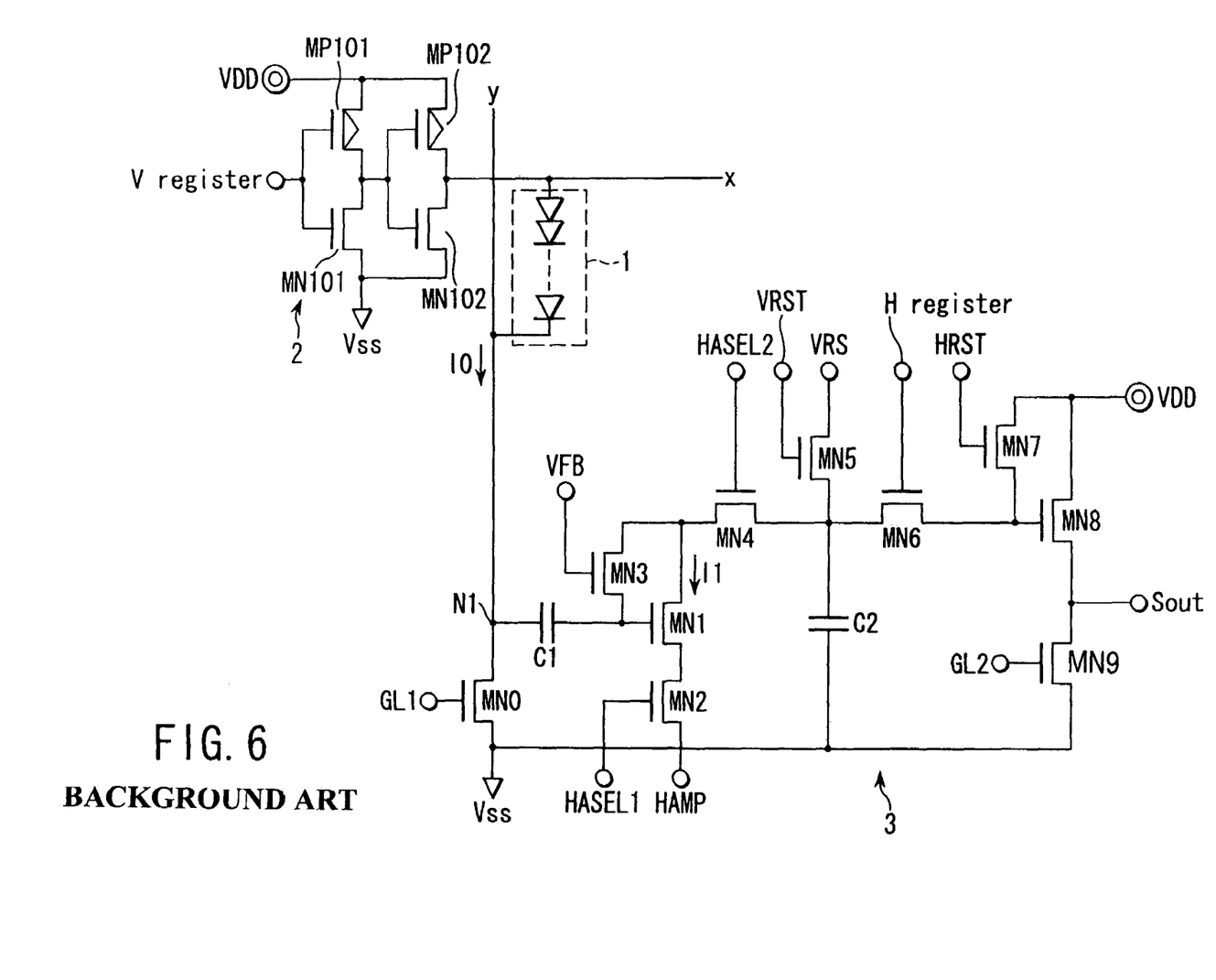
FIG. 6 is a circuit diagram showing the measurement circuit of an infrared sensor as a comparative example of the sensor device according to the embodiment.

FIG. 6 shows a comparative example of the sensor device according to the embodiment. FIG. 6 is a circuit diagram showing the arrangement of a conventional typical sensor device (a measurement circuit with a focus on one infrared sensor 1 of the sensor array). The sensor 1 has a plurality of diodes connected in series, as described above. The infrared sensor 1 is arranged at the intersection between row and column selection lines x and y. The anode of the diode is connected to one selection line (driving line) x. The cathode is connected to the other selection line (output signal line) y.

A driver 2 which is driven by the output "V register" of the vertical scanning register is connected to the driving line x. In the selection mode, a current is supplied from a PMOS transistor MP102 to the sensor 1. The terminal N1 of the output signal line y is grounded through an NMOS transistor MN0 (i.e., Vss=0). The terminal N1 is connected to the gate of a sense NMOS transistor MN1 of a detection circuit 3 through a coupling capacitor C1. The sense NMOS transistor MN1 executes operation for discharging a storage capacitor C2 in accordance with the sensor output. A change in voltage by the discharge of the storage capacitor C2 is extracted as an output Sout by a voltage follower formed from NMOS transistors MN8 and MN9.

The measurement operation will be briefly described. Before selection of the sensor 1, the storage capacitor C2 is charged with a constant voltage VRS through an NMOS transistor MN5. NMOS transistors MN3, and MN2 are turned on to apply a positive voltage from a terminal HAMP to the source of the sense NMOS transistor MN1 to charge the gate of the sense NMOS transistor MN1. After that, the gate is set in the floating state. More specifically, initial setting is done for the sense NMOS transistor MN1 to gate-bias the sense NMOS transistor MN1 to a condition for pentode operation.

In this state, when the sensor 1 is selected, the gate voltage Vg of the sense NMOS transistor MN1 changes in correspondence with the voltage drop Vf of the diode. When the NMOS transistor MN4 is turned on, the storage capacitor C2 is discharged by the sense NMOS transistor MN1 to decrease the potential. Hence, when charges remaining in the capacitor C2 are read through a selection NMOS transistor MN6 and the voltage follower, the temperature can be measured.

Figure 7:
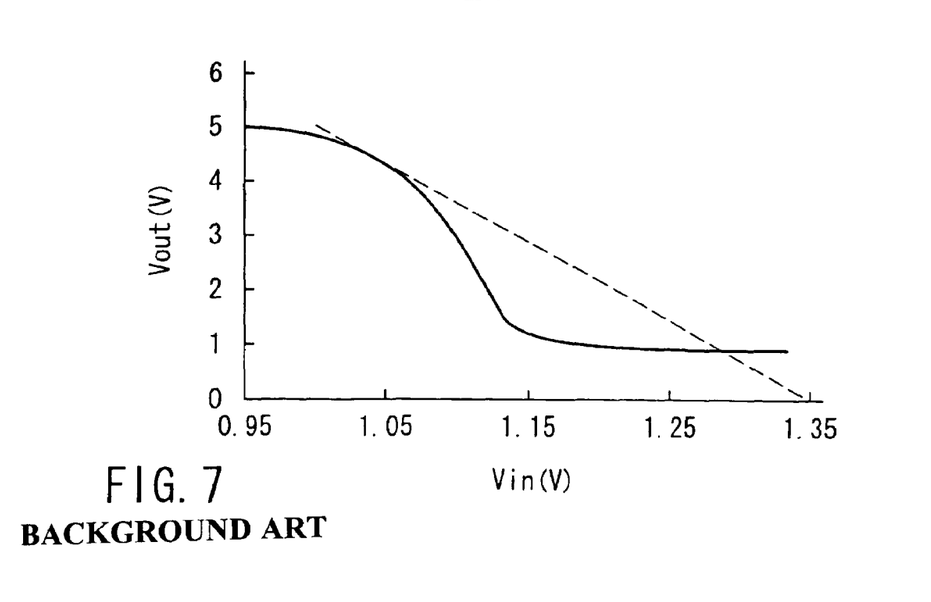
FIG. 7 is a graph showing the output voltage vs. input voltage characteristic of the infrared sensor shown in FIG. 6.

FIG. 7 shows the relationship between the input voltage Vin of the sense NMOS transistor MN1 and the output voltage Vout of the storage capacitor C2 of the conventional sensor device shown in FIG. 6, which is indicated by the solid line. The gradient of the voltage vs. current curve shown in FIG. 7 represents the temperature sensitivity. As is apparent from FIG. 7, the sensitivity is low in a region where the temperature change is small (a region where the input voltage Vin is low). When the input voltage becomes high, the output voltage Vout is saturated, and the sensitivity becomes low. Hence, the dynamic range becomes narrow. Preferably, a predetermined sensitivity is obtained in a wide input voltage range, as indicated by the broken line in FIG. 7.

The structure of the above-described conventional sensor device and that of the sensor device according to this embodiment are mainly different in the following two points.

The first point is the presence/absence of a mechanism which linearly controls the discharge of the storage capacitor C2 to achieve high sensitivity and wide dynamic range of the sensor device.

More specifically, in the conventional sensor device, high sensitivity is not obtained in a wide voltage range, as described above. This is mainly because the storage capacitor C2 is directly discharged by the sense NMOS transistor MN1. As described above, the sense NMOS transistor MN1 executes pentode operation, and the discharge current I1 is determined by almost the square of the input gate voltage. The voltage drop Vf of the diode changes only by several hundred μV, and the change in input gate voltage is also small. Hence, no large change in discharge current I1 can be obtained by one sense NMOS transistor MN1.

To the contrary, in the sensor device of this embodiment, as described above, the sense NMOS transistor MN1 is connected to the current source load PMOS transistor MP1 to form the sense amplifier circuit 31 instead of directly discharging the capacitor C2. The output current I1 is converted into a voltage by the current-to-voltage conversion circuit 32 using a current mirror, thereby driving the discharging circuit 33. Hence, the output voltage can linearly be changed in a wide input voltage range, and a wide dynamic range can be ensured.

To realize high sensitivity and a wide dynamic range in the conventional sensor device, the capacitance of the storage capacitor C2 may be adjusted. That is, when the capacitance of the storage capacitor C2 is decreased, a high sensitivity can be obtained in a narrow input voltage range. However, if the input voltage becomes high, the output voltage is readily saturated. Similarly, when the capacitance of the storage capacitor C2 is increased, saturation of the output voltage can be prevented in a wide input voltage range. However, this would sacrifice the sensitivity in a narrow input voltage range.

To the contrary, in the sensor device according to this embodiment, the discharge current I3 is linearly controlled by the resistance R and the voltage obtained by the current-to-voltage conversion circuit 32 using a current mirror. Hence, the linearity of the sensor output can be improved without increasing the capacitance of the capacitor C2, and high sensitivity and a wide dynamic range can be realized.

The second point is the presence/absence of a feedback system which removes the influence of a leakage current generated in the charging circuit for charging the storage capacitor C2. More specifically, in the conventional measurement circuit, when the potential of the storage capacitor C2 decreases due to discharging, the leakage current of the NMOS transistor MN5 increases. This leakage current impedes the voltage drop of the storage capacitor C2. For this reason, the output voltage saturation value in a high input voltage region does not sufficiently decrease.

In the sensor device according to this embodiment, when the voltage at the terminal N4 of the capacitor C2 decreases, the leakage current of the charging NMOS transistor MN5 increases and impedes the voltage drop at the terminal N4, as in the conventional circuit. However, the sensor device of this embodiment has a feedback system. Hence, when the voltage at the terminal N4 decreases due to the influence of the leakage current, the conductance of the NMOS transistor MN12 decreases to raise the voltage at the terminal N3, as described above. By the function of this feedback system, the discharge current of the capacitor C2 by the discharging circuit 33 is increased, and the voltage drop at the terminal N4 is accelerated. Accordingly, the voltage at the terminal N4 of the capacitor C2 can be lowered to sufficiently low level even in a high input voltage region. Hence, the dynamic range can be widened.

Figure 8:
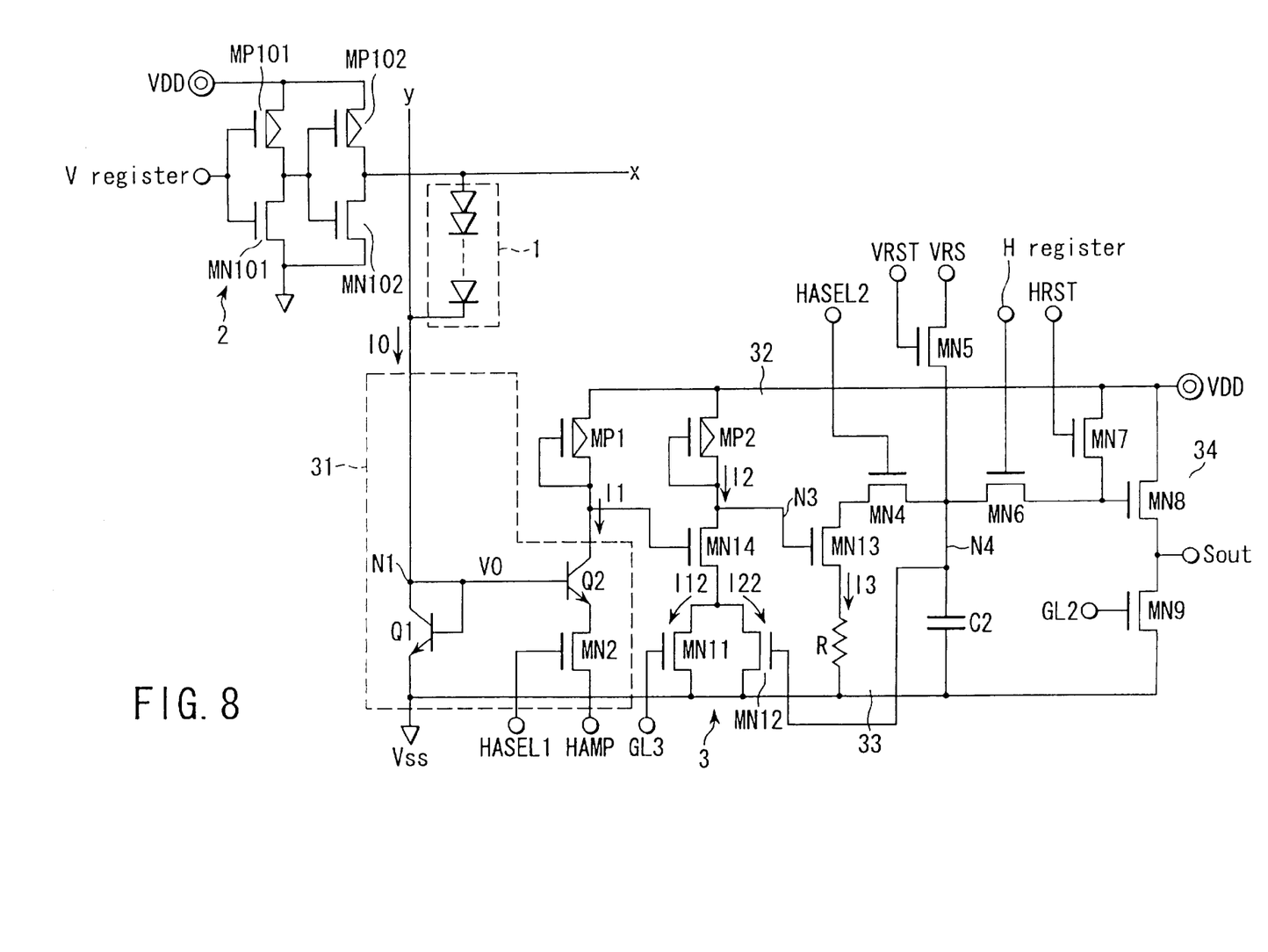
FIG. 8 is a circuit diagram of a measurement circuit according to another embodiment of the present invention.

FIG. 8 shows another embodiment in which the arrangement of a sense amplifier circuit 31 shown in FIG. 1 is modified. In this embodiment, bipolar transistors are used in the sense amplifier circuit 31. An npn transistor Q1 whose base and collector are connected to an output signal line y and emitter grounded operates as a diode which converts a sensor current I0 obtained on the output signal line y into a voltage V0. The voltage V0 is converted into a current I1 by an npn transistor Q2 which constitutes a current mirror circuit together with the transistor Q1 and a current source PMOS transistor MP1 connected to the collector of the npn transistor Q2.

A current-to-voltage conversion circuit 32 has an NMOS transistor MN14 whose gate is driven by the collector of the transistor Q2, a current source PMOS transistor MP2 arranged on the drain side of the NMOS transistor MN14, and NMOS transistors MN11 and MN12 which are juxtaposed on the source side as a load element.

In this embodiment, no constant current source NMOS transistor MN0 is used, unlike the above embodiment. A change in diode current I0 in a sensor 1, which is caused by an increase ΔTd in diode temperature due to incidence of infrared rays, is directly extracted as a change in voltage of the transistor Q1, i.e., a change in collector/emitter current I0 of the transistor Q2. For this reason, the voltage drop of the diode of the sensor 1 need not be detected. Hence, diodes need not be connected in series. Accordingly, the area of the sensor 1 can be reduced. In addition, the power supply voltage of a driver 2 can be made low, and power consumption can be reduced.

The n-type collector layer 21 of this embodiment also outputs the output current I1 in response to the change in output current I0. The current I1 is converted into a voltage by a current-to-voltage conversion circuit 32, as in the above embodiment, to control a discharging circuit 33. Even in the circuit of this embodiment, the change in output current I0 and the change in charge amount of the capacitor C2 have an excellent linearity due to the same reason as in the above embodiment.

Figure 9A:
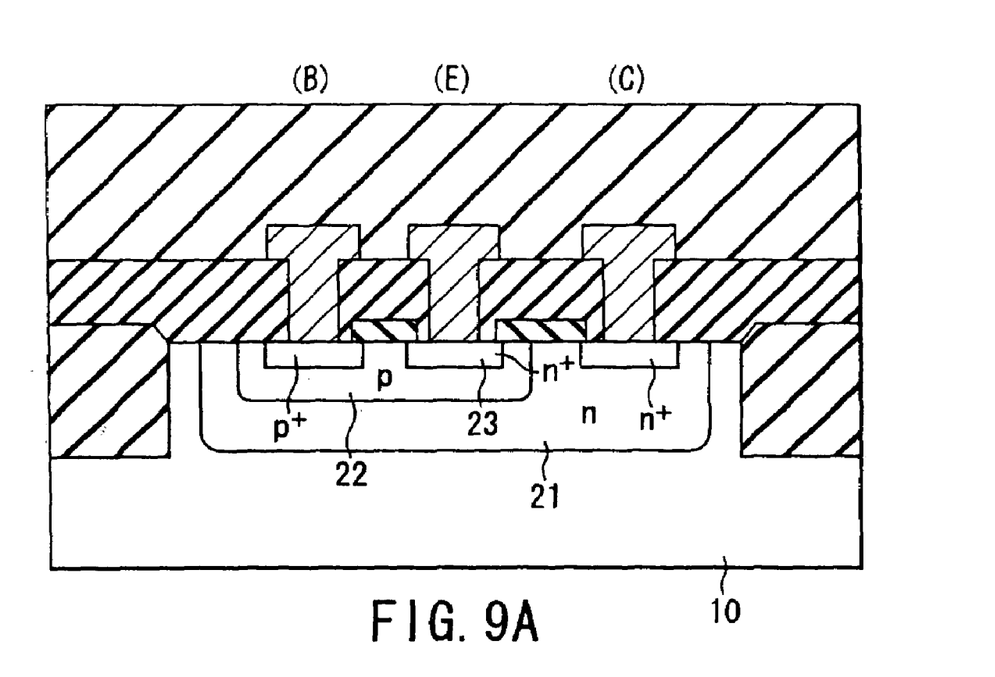
FIG. 9A is a sectional view showing a structure of a bipolar transistor used in the measurement circuit shown in FIG. 8.
Figure 9B:
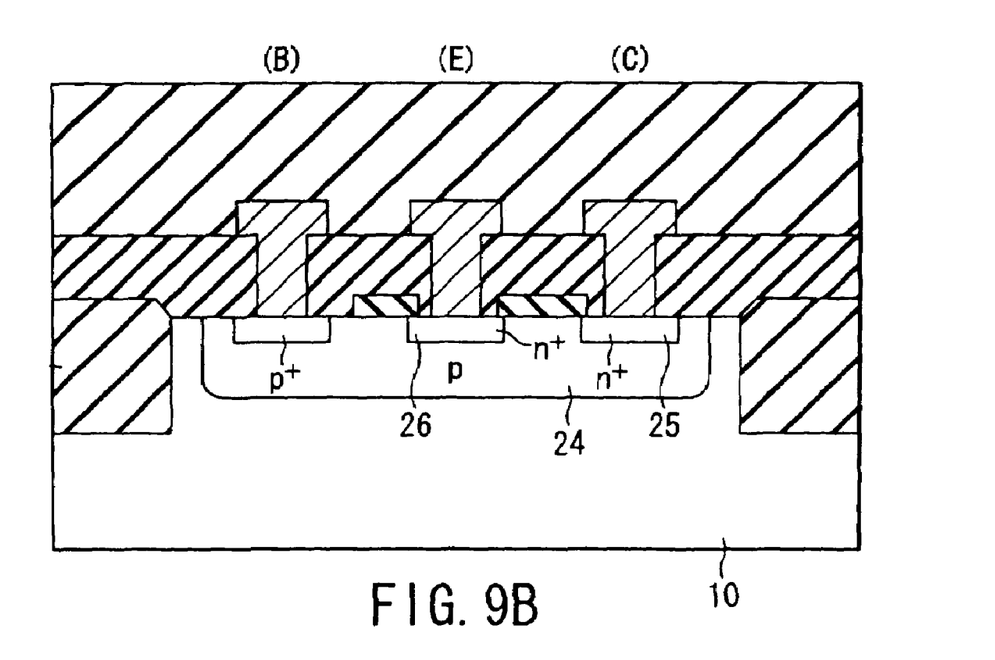
FIG. 9B is a sectional view showing another structure of the bipolar transistor used in the measurement circuit shown in FIG. 8.

The bipolar transistors Q1 and Q2 used in the sense amplifier circuit 31 of this embodiment can be formed in a structure shown in FIG. 9A or 9B on the same substrate 10 as that of the sensor array. FIG. 9A shows a vertical transistor having an n-type collector layer 21, a p-type base layer 22 formed in the n-type collector layer 21, and an n$^+$-type emitter layer 23 formed in the p-type base layer 22. FIG. 9B shows a lateral transistor having an n$^+$-type collector layer 25 and n$^+$-type emitter layer 26 formed in a p-type base layer 24.

Figure 10:
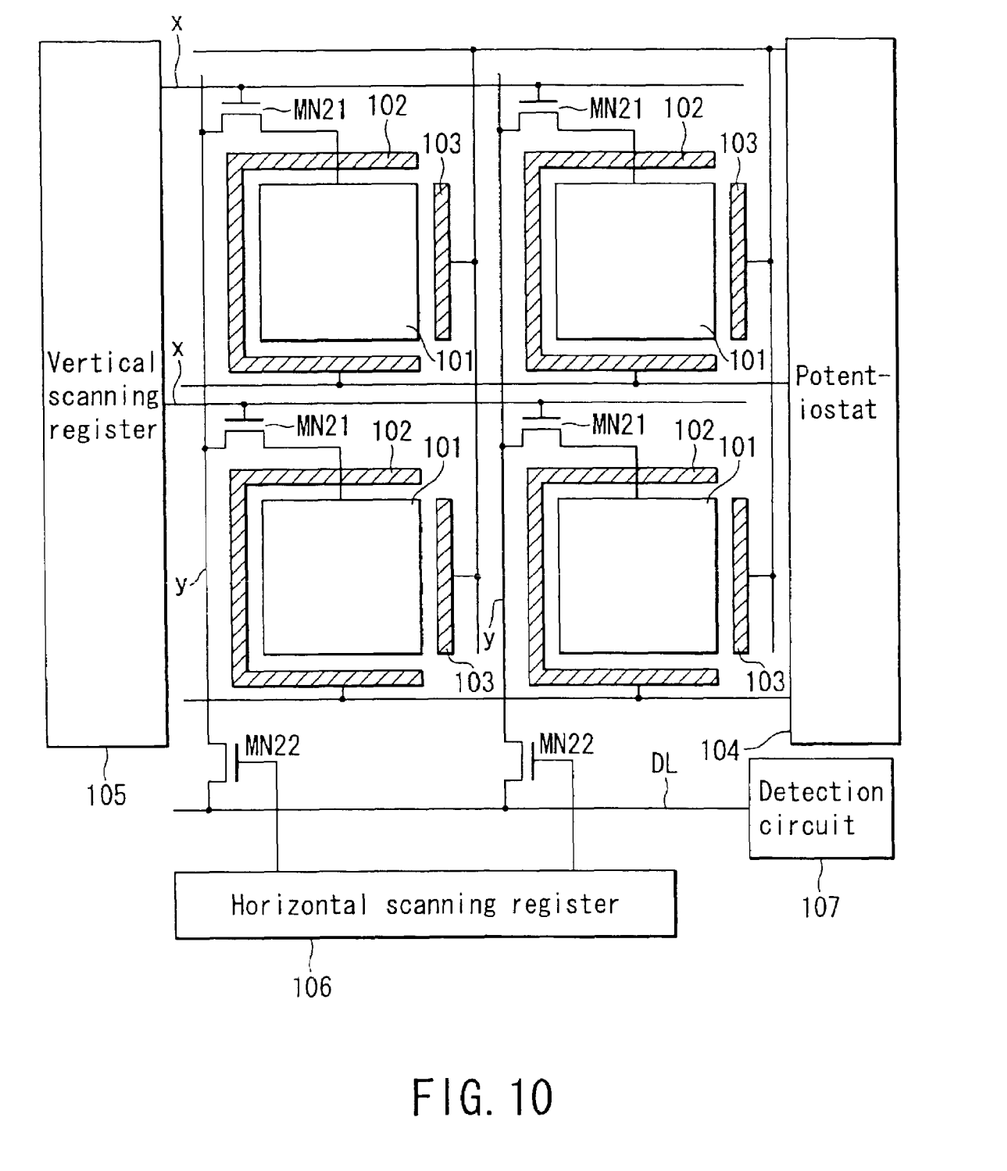
FIG. 10 is a view showing the arrangement of a DNA sensor to which the sensor device according to the embodiment of the present invention is applied.

In the above embodiments, a non-cooled infrared sensor has been described as a sensor array. However, the circuit of the present invention can also be applied to various kinds of sensors. For example, FIG. 10 shows a sensor device for detecting nucleic acid such as DNA. A DNA sensor (DNA chip) is used to detect the base sequences of genes. The structures of DNA sensors are described in detail in, e.g., U.S. Pat. Nos. 5,776,672 and 5,972,692.

As shown in FIG. 10, each cell has a probe electrode 101, a counter electrode 102 opposing three sides of the probe electrode 101, and a reference electrode 103 opposing the remaining side of the probe electrode 101. Probe electrode 101 is connected to row and column signal lines x and y through transistor MN21. Column signal line y is connected to the data line DL and the horizontal scanning register 106 through transistor MN22. The sensor is set in a solution. A voltage is applied to the counter electrode 102 and reference electrode 103 by a potentiostat 104, so that the voltage between the probe electrode 101 and the reference electrode 103 can be fixed. Various kinds of DNA probes in a single-strand state are bonded to the probe electrode 101. A target DNA is dropped. When the specimen DNA has the same base sequence as that of a DNA probe, a double strand is formed. Using this fact, the specimen DNA is determined.

Figure 11:
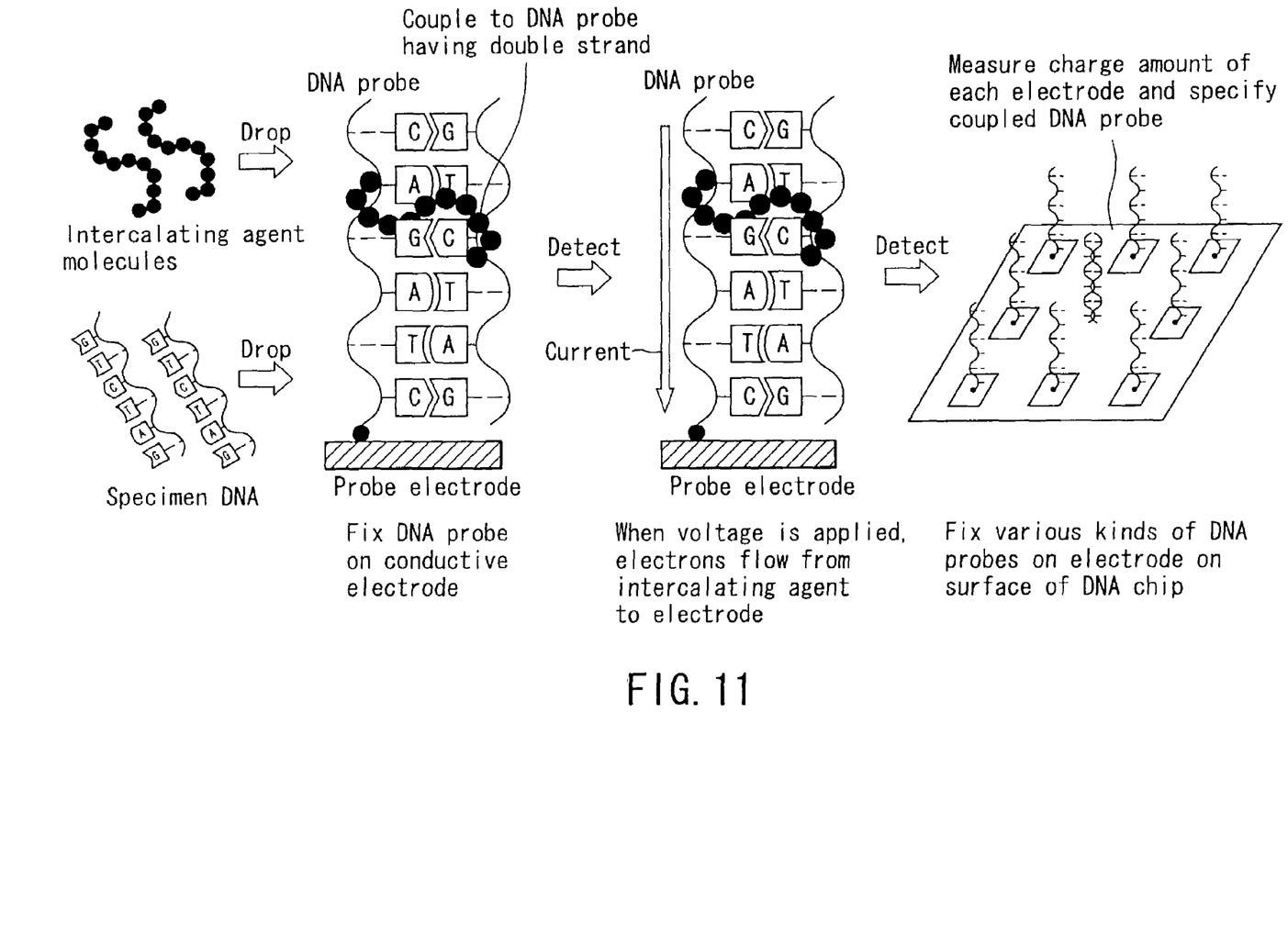
FIG. 11 is a view for explaining the operation principle of the DNA sensor shown in FIG. 10.

More specifically, as shown in FIG. 11, when a target DNA is dropped on the DNA probes bonded to the probe electrode 101, and the target DNA has the same base sequence as that of a DNA probe, the target DNA is hybridized to the probe DNA and a double strand is formed. In addition, when a kind of intercalating agent is added, it couples to the double strand. In this state, a voltage is applied to the probe electrode 101 of the cell selected by a vertical scanning register 105 and horizontal scanning register 106, electrons flow from the intercalating agent to the probe electrode due to the electrochemical reaction. Hence, a current flows.

Accordingly, an output current flows to the signal line y selected by the horizontal scanning register 106 from the row and column signal lines x and y shown in FIG. 10. When this output current is detected by a detection circuit 107 connected to a data line DL, the specimen DNA can be determined. When the output current extracted from the data line DL is defined as the current I1 shown in FIG. 1 or 8, and the detection circuit 107 has the same arrangement as that of the detection circuit 3 described in FIG. 1 or 3, highly accurate measurement can be executed.

In the embodiment described above, the storage capacitor C2 is discharged when a voltage drop occurs in the sensor 1, and the charge remaining in the capacitor C2 is then read to detect the infrared image. Alternatively, the capacitor C2 may be first completely discharged and then be charged when a voltage drop occurs in the sensor 1. Then, the charge accumulated in the capacitor C2 results in a voltage, which is read to from an infrared image. In this case, the sensor device is controlled by setting the ground and reset potentials of the capacitor C2 at negative values. By virtue of this control, the current I3 controlled as the NMOS transistor 13 FIG. 1 is opened and closed flows in a direction opposite to the direction in which it flows in the above embodiment. Hence, a sensor device of recharged type can be provided.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A sensor device which detects a physical change amount or chemical change amount, comprising:
   a sensor array including a plurality of sensors, the sensor array configured to detect the physical change amount or chemical change amount and to output an electrical signal;
   a sense amplifier circuit configured to amplify the electrical signal to generate an amplified electrical signal;
   a current transfer circuit configured to include a first stage and a second stage, and to transfer a first current appearing on the first stage on a basis of the amplified electrical signal to the second stage as a second current;
   a current-to-voltage conversion circuit configured to convert the second current to a first voltage;
   a first discharging/charging circuit including a capacitor and a first load element connected to the capacitor, said first discharging/charging circuit configured to discharge/charge electric charges from/to the capacitor through the first load element on a basis of the first voltage; and
   an output circuit configured to output a change in voltage occurring on the capacitor according to discharging/charging of the electric charges.

2. The device according to claim 1, further comprising:
   a second discharging/charging circuit configured to charge/discharge the electric charges to/from the capacitor; and
   a control circuit configured to control the current-to-voltage conversion circuit on the basis of a potential at a node between the capacitor and the second discharging/charging circuit.

3. The device according to claim 1, wherein
   the sense amplifier circuit includes a load MOS transistor configured to be electrically connected to the sensor array and biased to a pentode region so as to convert the electrical signal into a second voltage and a sense MOS transistor having a gate configured to receive the second voltage;
   the current transfer circuit comprises a current mirror which includes a first current source load transistor and a second current source load transistor, the first current source load transistor configured to be connected to a drain of the sense MOS transistor and to construct the first stage, and the second current source load transistor configured to construct the second stage; and
   the current-to-voltage conversion circuit includes a second load element configured to be supplied with the second current.

4. The device according to claim 3, wherein the second load element includes a first NMOS transistor configured to be applied with a fixed gate bias, and a second NMOS transistor which is connected in parallel to the first NMOS transistor and includes a gate configured to be driven on the basis of a terminal voltage of the capacitor.

5. The device according to claim 1, wherein
   the sense amplifier circuit includes a first bipolar transistor that includes a collector and base, the collector and base each configured to be electrically connected to the sensor array, an emitter configured to be connected to a reference potential and to convert the electrical signal into a second voltage, and a second bipolar transistor which comprises a current mirror together with the first bipolar transistor;
   the current transfer circuit includes a first current source load transistor connected to a collector of the second bipolar transistor, a first NMOS transistor having a gate connected to the collector of the second bipolar transistor and a second current source load transistor connected to a drain of the first NMOS transistor and constitutes a current mirror together with the first current source load transistor; and
   the current-to-voltage conversion circuit includes a second load element connected to a source of the first NMOS transistor.

6. The device according to claim 5, wherein the second load element includes a second NMOS transistor to which a fixed gate bias is applied, and a third NMOS transistor which is connected in parallel to the second NMOS transistor and includes a gate driven on the basis of a terminal voltage of the capacitor.

7. The device according to claim 1, wherein
   the first discharging/charging circuit includes a discharge/charge transistor whose gate is configured to be driven by an output from the current-to-voltage conversion circuit; and
   the first load element is a resistance connection between a source of the discharge/charge transistor and a reference potential terminal.

8. The device according to claim 1, wherein each of the plurality of sensors is an infrared sensor configured to use a diode as a thermoelectric conversion element.

9. The device according to claim 1, wherein each of the plurality of sensors is a DNA sensor configured to output a current due to electrochemical reaction between a DNA probe and a specimen DNA.

10. A sensor device configured to detect a physical change amount or chemical change amount as an electrical signal, comprising:
a sensor array including a plurality of sensors, the sensor array configured to detect the physical change amount or chemical change amount and to output the electrical signal;
a capacitor;
a first discharging/charging circuit configured to be driven by a driving voltage based on the electrical signal of the sensor array so as to discharge/charge electric charges from/to the capacitor;
a second discharging/charging circuit configured to charge/discharge the electric charges to/from the capacitor;
a control circuit configured to control the driving voltage on the basis of a potential at a node between the capacitor and the second discharging/charging circuit; and
an output circuit configured to output a change in voltage occurring on the capacitor according to discharging/charging of the electric charges.

11. The device according to claim 10, wherein each of the plurality of sensors is an infrared sensor configured to use a diode as a thermoelectric conversion element.

12. The device according to claim 10, wherein each of the plurality of sensors is a DNA sensor configured to output a current due to electrochemical reaction between a DNA probe and a specimen DNA.

13. A sensor device which detects a physical change amount or chemical change amount, comprising:
a sensor array including a plurality of sensors, the sensor array configured to detect the physical change amount or chemical change amount and to output an electrical signal;
a sense amplifier circuit configured to amplify the electrical signal to generate an amplified electrical signal;
a current transfer circuit configured to include a first stage and a second stage, and to transfer a first current appearing on the first stage on a basis of the amplified electrical signal to the second stage as a second current;
a current-to-voltage conversion circuit configured to convert the second current to a first voltage;
a first discharging/charging circuit including a capacitor and a first load element connected to the capacitor, said first discharging/charging circuit configured to discharge/charge electric charges from/to the capacitor through the first load element on a basis of the first voltage;
a second discharging/charging circuit configured to charge/discharge the capacitor;
a control circuit configured to control the current-to-voltage conversion circuit on the basis of a potential at a node between the capacitor and the first discharging/charging circuit; and
an output circuit configured to output a change in voltage occurring on the capacitor according to discharging/charging of the electric charges.

14. The device according to claim 13, wherein
the sense amplifier circuit includes a load MOS transistor configured to be electrically connected to the sensor array and biased to a pentode region which converts the electrical signal into second voltage and a sense MOS transistor having a gate configured to receive the second voltage;
the current transfer circuit comprises a current mirror which includes a first current source load transistor and a second current source load transistor, the first current source load transistor configured to be connected to a drain of the sense MOS transistor and to construct the first stage, and the second current source load transistor configured to construct the second stage; and
the current-to-voltage conversion circuit includes a second load element configured to to be supplied with the second current.

15. The device according to claim 14, wherein the second load element includes a first NMOS transistor configured to be applied with a fixed gate bias, and a second NMOS transistor connected in parallel to the first NMOS transistor, said second NMOS transistor includes a gate configured to be driven on a basis of a terminal voltage of the capacitor.

16. The device according to claim 13, wherein
the sense amplifier circuit includes a first bipolar transistor that includes a collector and base, said collector and base each configured to be electrically connected to the sensor array, an emitter configured to be connected to a reference potential and to convert the electrical signal into a second voltage, and a second bipolar transistor which comprises a current mirror together with the first bipolar transistor;
the current transfer circuit includes a first current source load transistor connected to a collector of the second bipolar transistor, a first NMOS transistor having a gate connected to the collector of the second bipolar transistor and a second current source load transistor which is connected to a drain of the first NMOS transistor and constitutes a current mirror together with the first current source load transistor; and
the current-to-voltage conversion circuit includes a second load element connected to a source of the first NMOS transistor.

17. The device according to claim 16, wherein the second load element includes a second NMOS transistor configured to be applied with a fixed gate bias, and a third NMOS transistor which is connected in parallel to the second NMOS transistor and includes a gate configured to be driven on the basis of a terminal voltage of the capacitor.

18. The device according to claim 13, wherein the first discharging/charging circuit includes a discharge/charge transistor whose gate is configured to be driven by an output from the current-to-voltage conversion circuit, and
the first load element is a resistance connection between a source of the discharge/charge transistor and a reference potential terminal.

19. The device according to claim 13, wherein each of the plurality of sensors is an infrared sensor configured to use a diode as a thermoelectric conversion element.

20. The device according to claim 13, wherein each of the plurality of sensors is a DNA sensor configured to output a current due to electrochemical reaction between a DNA probe and a specimen DNA.

* * * * *